| United States Patent [19] | [11] Patent Number: 5,428,090 |
|---|---|
| Ogawa et al. | [45] Date of Patent: Jun. 27, 1995 |

[54] POLYCARBONATE POLYMER DERIVED FROM DIHYDROXY COMPOUND HAVING TRIPHENYLAMINE STRUCTURE AND PROCESS FOR PRODUCING THE SAME

[75] Inventors: Noriyoshi Ogawa; Toshiaki Takata, both of Osaka; Satoshi Kanayama, Kanagawa, all of Japan

[73] Assignee: Mitsubishi Gas Chemical Co., Inc., Tokyo, Japan

[21] Appl. No.: 194,219

[22] Filed: Feb. 9, 1994

[30] Foreign Application Priority Data

Feb. 9, 1993 [JP] Japan .................................. 5-021325
Feb. 9, 1993 [JP] Japan .................................. 5-021329

[51] Int. Cl.$^6$ .............................................. C08G 64/06
[52] U.S. Cl. ................................ 528/203; 252/182.24; 252/182.26; 252/182.34; 528/196; 528/199; 528/204; 528/298
[58] Field of Search ............... 528/199, 196, 298, 203, 528/204; 252/182.24, 182.26, 182.34

[56] References Cited

U.S. PATENT DOCUMENTS

| 4,935,487 | 6/1990 | Yanus et al. ........................ 528/203 |
| 4,937,165 | 6/1990 | Ong et al. . |
| 5,011,906 | 4/1991 | Ong et al. ........................... 528/203 |

*Primary Examiner*—Joseph L. Schofer
*Assistant Examiner*—John M. Cooney, Jr.
*Attorney, Agent, or Firm*—Sughrue, Mion, Zinn, Macpeak & Seas

[57] ABSTRACT

A polycarbonate derived from a novel dihydroxy compound having a triphenylamine structure, and a process for producing the polycarbonate are disclosed. The polycarbonate is obtained by reacting a dihydroxy compound having a triphenylamine structure described hereinbefore and a carbonate precursor, or by reacting the dihydroxy compound, a dihydric phenol compound and the carbonate precursor. The polycarbonate is useful as a plastic molding material or as a material for forming a polymer alloy with other resin.

14 Claims, No Drawings

POLYCARBONATE POLYMER DERIVED FROM DIHYDROXY COMPOUND HAVING TRIPHENYLAMINE STRUCTURE AND PROCESS FOR PRODUCING THE SAME

FIELD OF THE INVENTION

The present invention relates to a polycarbonate polymer derived from a novel dihydroxy compound having a triphenylamine structure and a process for producing the same. More specifically, the present invention relates to a polycarbonate polymer of a novel structure having a triphenylamine structure in a repeating unit, and the polycarbonate polymer is obtained by reacting a dihydroxy compound having a triphenylamine structure described hereinbelow and a carbonate precursor or by reacting the dihydroxy compound, a dihydric phenol compound, and the carbonate precursor.

The polycarbonate polymer of the present invention is useful as a plastic molding material or as a material for forming a polymer alloy with another resin.

BACKGROUND OF THE INVENTION

Polycarbonates industrially produced at present are mostly so-called bisphenol-type polycarbonates produced using bisphenol A [2,2-bis(4-hydroxyphenyl)propane] as the raw material. A bisphenol-type polycarbonate is a resin well-balanced in the physical properties of the resin, such as heat resistance, mechanical strength, etc.

Recently, with the increase of the uses of polycarbonates, polycarbonates having excellent properties have been desired and according to the desire, polycarbonates having various structures have been developed as described in, e.g., JP-A-63-108023 and JP-A-64-66236 (the term "JP-A" as used herein means an "unexamined published Japanese patent application").

Furthermore, in the point of physical properties, the development of polycarbonates having specific properties or polycarbonates having more excellent properties in connection with the field of use has been strongly desired in the marketplace.

SUMMARY OF THE INVENTION

Accordingly, one object of the present invention is to provide a novel polycarbonate having a specific structure and being useful as a material for forming a polymer alloy with another resin or as a material for a photosensitive material.

Another object of the present invention is to provide a polycarbonate having a repeating unit derived from a novel dihydroxy compound having a triphenylamine structure.

A still another object of the present invention is to provide a novel dihydroxy compound having a triphenylamine structure, which constitutes the polycarbonate of the present invention.

Further object of the present invention is to provide a process for producing the polycarbonate.

The polycarbonate of the present invention is obtained by reacting the dihydroxy compound having the triphenylamine structure and a carbonate precursor or by reacting the dihydroxy compound, a dihydric phenol, and the carbonate precursor.

It has now been found that the above-described objects can be attained by the present invention described hereinbelow.

According to one embodiment of the present invention, there is provided a polycarbonate comprising a repeating unit represented by the following formula (A) derived from a dihydroxy compound having a triphenylamine structure represented by the following formula (D) or a polycarbonate comprising the repeating unit represented by the following formula (A) and a repeating unit represented by the following formula (C) derived from a dihydric phenol compound represented by the following formula (E), wherein the molar ratio of the repeating unit represented by the following formula (A) in the polycarbonate is $0<(A)/[(A)+(C)]\leq 1$;

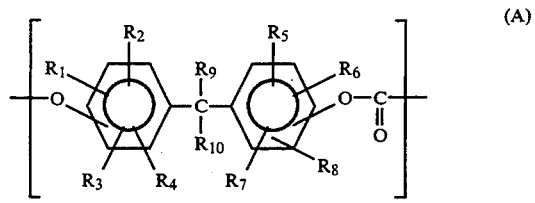

wherein $R_1$ to $R_8$ each represents hydrogen atom, a halogen atom, an alkoxy group, an alkyl group which may have a substituent, an alkenyl group which may have a substituent, or an aryl group which may have a substituent and one of $R_9$ and $R_{10}$ represents a group containing a triphenylamine represented by the following formula (B) and the other thereof represents hydrogen atom, an alkyl group, an alkenyl group, or an aryl group, each group may have a substituent, or both of $R_9$ and $R_{10}$ represent a group containing the triphenylamine represented by the following formula (B);

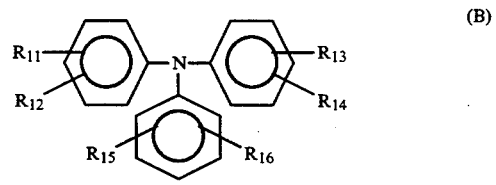

wherein $R_{11}$ to $R_{16}$ each represents hydrogen atom, a halogen atom, an alkyl group, an alkoxy group, an alkenyl group, an aryl group, an arylamino group, an aryl ether group, or an aminoaryl ether group, each group may have a substituent, or $R_{11}$ and $R_{12}$, $R_{13}$ and $R_{14}$, or $R_{15}$ and $R_{16}$ represent groups which combine with each other to form a carbon ring or a heterocyclic ring, and at least one of $R_{11}$ to $R_{16}$ becomes a divalent group and combines with $-(CH_2)_a-$ (wherein a represents an integer of from 0 to 5) to form a group shown by $R_9$ or $R_{10}$ of the formula (A) described above;

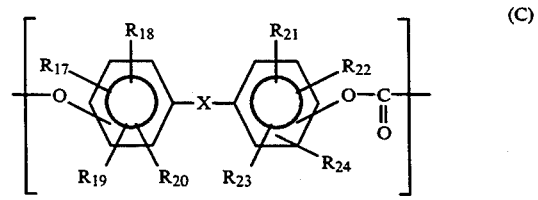

wherein $R_{17}$ to $R_{24}$ each represents hydrogen atom, a halogen atom, an alkyl group, or an aryl group, each group may have a substituent and X represents

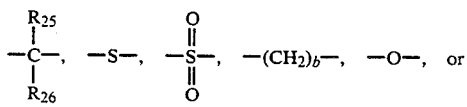

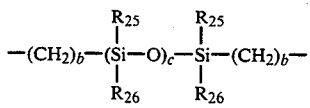

wherein R₂₅ and R₂₆ each represents hydrogen atom, a halogen atom, an alkyl group, or an aryl group, each group may have a substituent or R₂₅ and R₂₆ represent groups which combine with each other to form a carbon ring or a heterocyclic ring; b represents an integer of from 0 to 20; and c represents an integer of from 0 to 2,000;

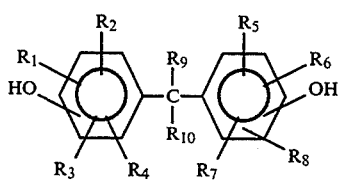

wherein $R_1$ to $R_{10}$ are the same as defined in the formula (A) described above;

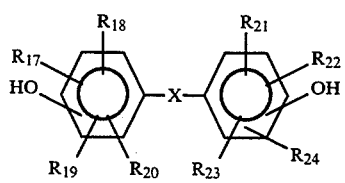

wherein $R_{17}$ to $R_{24}$ and X are the same as defined in the formula (C) described above.

According to another embodiment of the present invention, there is provided a process of producing the polycarbonate described above.

The polycarbonate comprising the repeating unit represented by the formula (A) described above or the polycarbonate having the triphenylamine structure typified by the copolymer comprising the repeating unit represented by the formula (A) and the repeating unit represented by the formula (C) can be, respectively, produced by reacting the dihydroxy compound represented by the formula (D) or by reacting the dihydroxy compound, the dihydric phenol compound represented by the formula (E), and a carbonate precursor.

DETAILED DESCRIPTION OF THE INVENTION

The present invention is described in detail below.

In the present invention, in the case of obtaining the copolymer comprising the repeating unit represented by the formula (A) and the repeating unit represented by the formula (C), the dihydroxy compound represented by the formula (D) and the dihydric phenol compound represented by the formula (E) can be used at an optional ratio, but it is preferred that the dihydroxy compound represented by the formula (D) is used in the proportion of from 99 to 1 mol % and the dihydric phenol compound represented by the formula (E) is used in the proportion of from 1 to 99 mol %.

In the dihydroxy compound represented by the formula (D), at least one of $R_9$ and $R_{10}$ is a compound having the triphenylamine structure represented by the formula (B) and each of $R_{11}$ to $R_{16}$ of the formula (B) becomes a divalent group and combines with an alkylene group represented by —(CH₂)$_a$— (wherein a is an integer of from 0 to 5) to form $R_9$ or $R_{10}$ of the formula (D).

The dihydroxy compound represented by the formula (D) described above can be obtained by reacting a phenol compound represented by the following formula (X) and a ketone or aldehyde compound represented by the following compound (Y) in the presence of an acidic catalyst such as hydrogen chloride, etc.

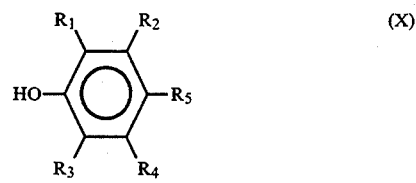

wherein $R_1$ to $R_5$ each represents hydrogen atom, a halogen atom, an alkoxy group, an alkyl group which can have a substituent, an alkenyl group which can have a substituent, or an aryl group which can have a substituent, with proviso that at least one of $R_1$ to $R_5$ is hydrogen atom;

wherein one of $R_9$ and $R_{10}$ represents a group having the triphenylamine structure represented by the formula (B) described above and the other thereof represents hydrogen atom, an alkyl group, an alkenyl group, or an aryl group, each group can have a substituent, or both of $R_9$ and $R_{10}$ represent the group having the triphenylamine structure represented by the formula (B).

Examples of the phenol compound represented by the formula (X) described above are phenol, o-cresol, m-cresol, p-cresol, o-chlorophenol, m-chlorophenol, p-chlorophenol, o-bromophenol, m-bromophenol, p-bromophenol, o-tert-butylphenol, 2,3-xylenol, 2,6-xylenol, 2,6-di-tert-butylphenol, o-phenylphenol, 2,6-dichlorophenol, 2,6-dibromophenol, 2,6-diethylphenol, 2,6-diisopropylphenol, eugenol, o-allylphenol, isoeugenol, thymol, m-methoxyphenol, guaiacol, o-fluorophenol, and p-tert-butylphenol. Of those compounds, the compounds which do not have a substituent at the para-position are preferred from the point of reactivity.

The ketone or aldehyde compound represented by the formula (Y) described above is a compound having the triphenylamine structure represented by the formula (B) described above. The examples are bis(4-methylphenyl)-4-formylphenylamine, bis(4-methylphenyl)-4-acetophenylamine, bis(4-methylphenyl)-4-acetylphenylamine, bis(4-methylphenyl)-4-(3-oxobutyl)-phenylamine, 1,3-bis[4-bis(4-methylphenyl)aminophenyl]-2-propane, 9,9-dimethyl-2-(N-phenyl-N-(4-acetylphenyl)aminofluorene, 4-(N-phenyl-N-(4-acetylphenyl) amino-4'-methylstilbene, and N-(4-acetylphenyl)-N,N-bis(4-biphenylyl)amine, and the like. The representative examples thereof are shown below.

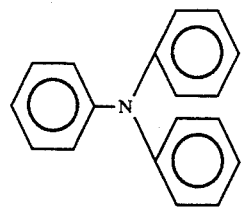
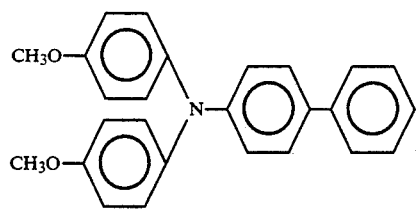
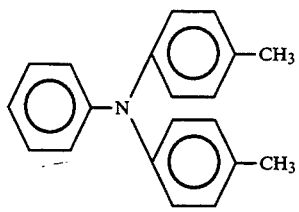
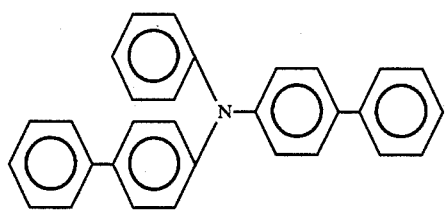
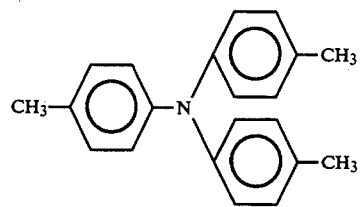
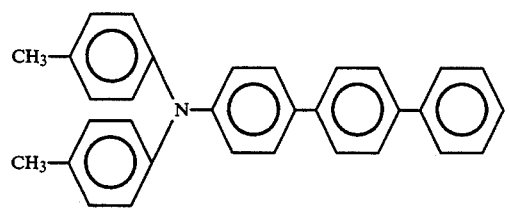
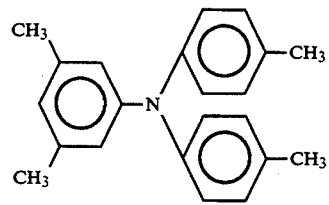
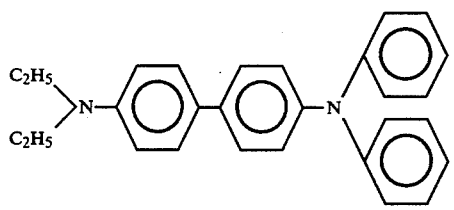
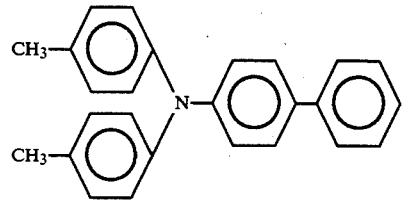
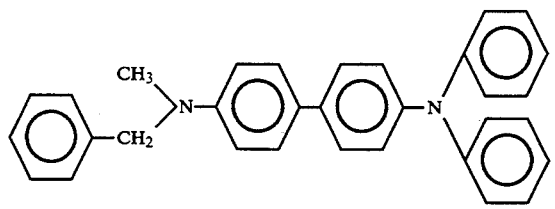
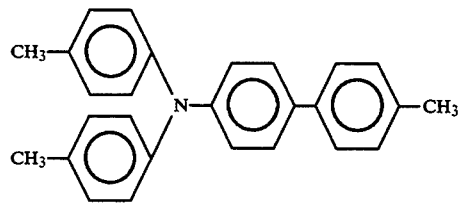
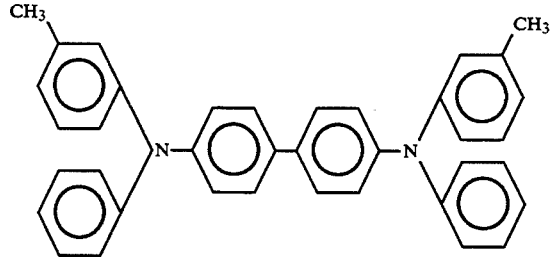
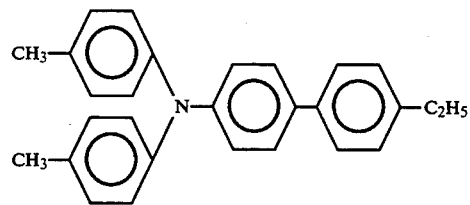
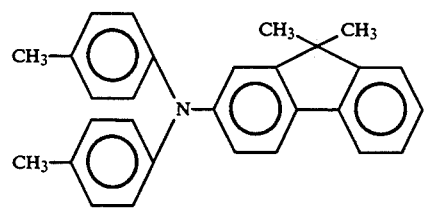

-continued
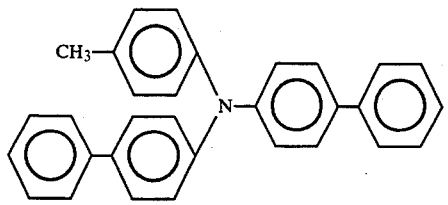
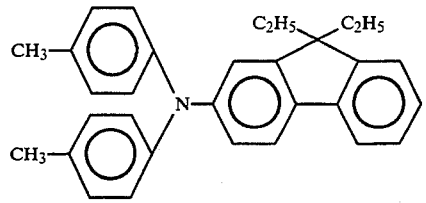
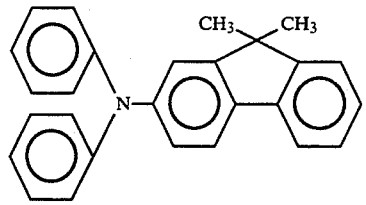
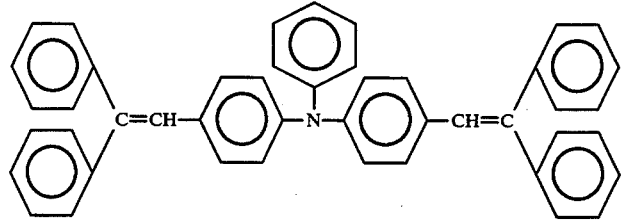
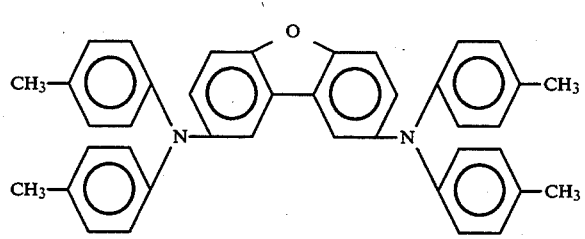
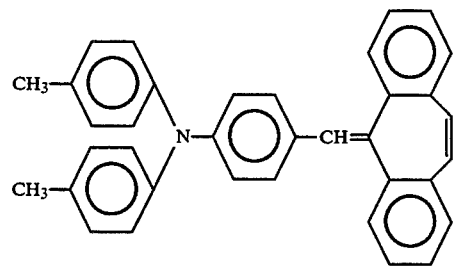
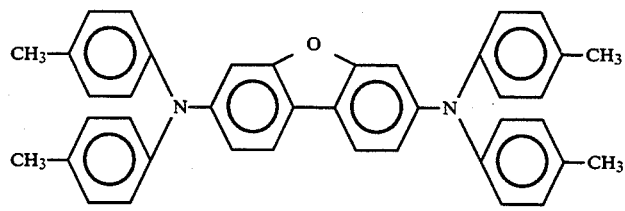

-continued
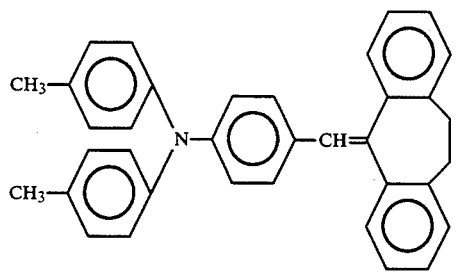
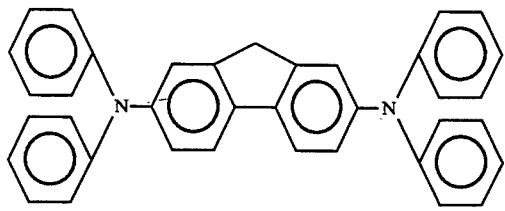
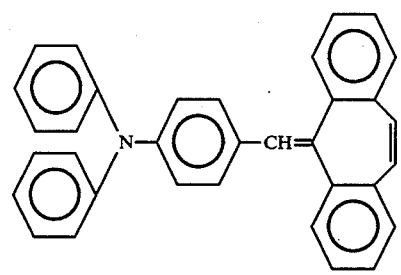
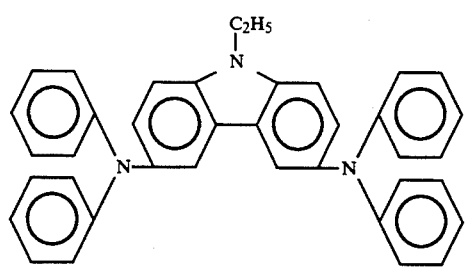
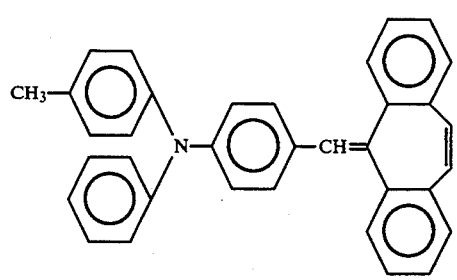
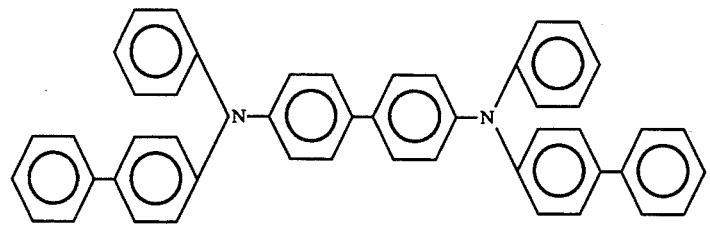
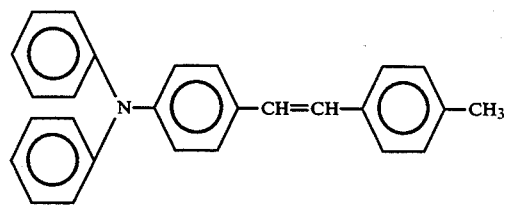
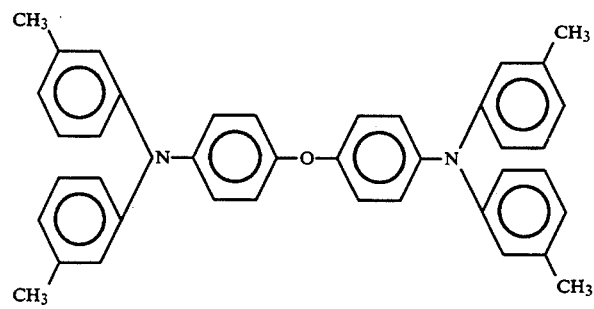

-continued

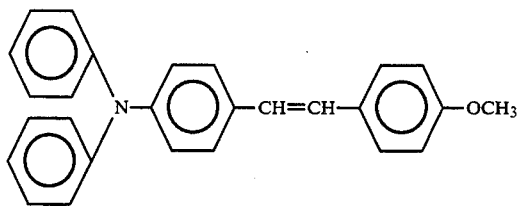

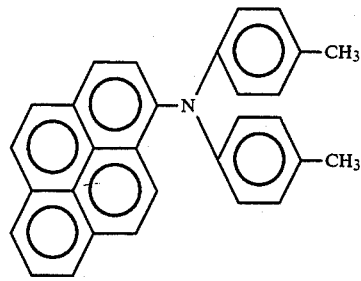
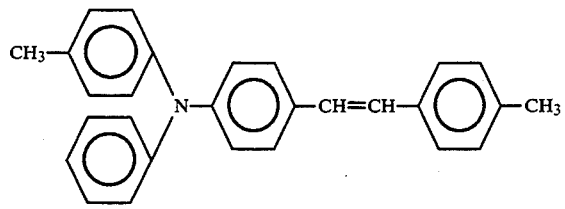

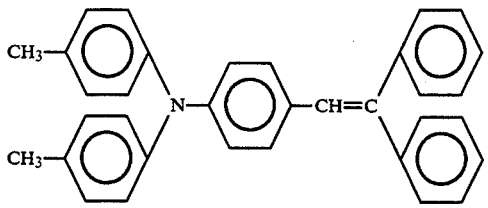
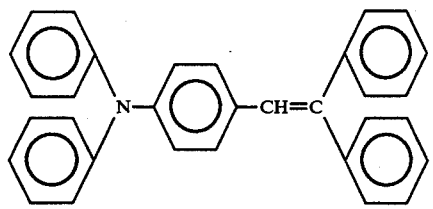

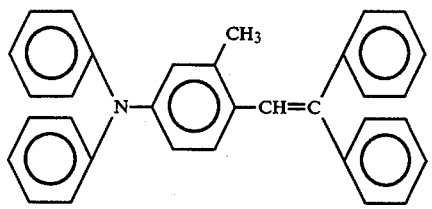
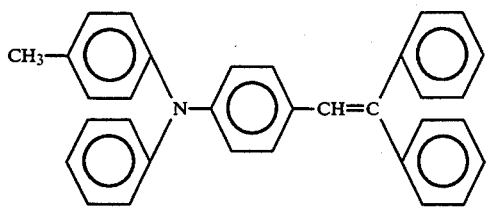

In the reaction of the phenol compound represented by the formula (X) described above and the ketone or aldehyde compound represented by the formula (Y) described above, the phenol compound is usually used in an excess amount to the ketone or aldehyde compound, and more practically from 3 to 30 mols of the phenol compound represented by the formula (X) is used to one mol of the ketone or aldehyde compound represented by the formula (Y).

The reaction of the phenol compound represented by the formula (X) described above and the ketone or aldehyde compound represented by the formula (Y) described above is conducted in the presence of an acidic catalyst, and if necessary, a solvent. The solvent which is preferably used is an inert solvent, for example, aromatic hydrocarbon solvents such as benzene, toluene, xylene, ethylbenzene, etc.

The catalyst which is used in the reaction is an acidic catalyst such as hydrogen chloride, sulfuric acid, toluenesulfonic acid, trifluoroacetic acid, trifluoromethanesulfonic acid, oxalic acid, phosphorus pentachloride, polyphosphoric acid, a strongly acidic cation exchange resin, etc. Of those catalysts, hydrogen chloride and the strongly acidic cation exchange resin are preferably used from the standpoints of the reaction acceleration and the post treatment.

The amount of the catalyst used differs according to the kind of the catalyst but in the case of using hydrogen chloride, the amount of the catalyst used is usually in the range of from 0.5 to 10% by weight based on the total weight of the phenol and the ketone or the aldehyde compound.

In the reaction, a compound having a mercapto group may be used as a promotor together with the acidic catalyst. Examples of the compound having a mercapto group are alkyl mercaptans such as methyl mercaptan, ethyl mercaptan, propyl mercaptan, butyl mercaptan, octyl mercaptan, dodecyl mercaptan, etc.; aromatic mercaptans such as thiophenol, etc.; and mercapto-organic acids such as mercaptoacetic acid, mercaptopropionic acid, etc.

The promotor is usually used in an amount of from 0.1 to 5% by weight based on the total weight of the phenol compound and the ketone or aldehyde compound.

The reaction temperature differs according to the kinds of the ketone or aldehyde compound and the catalyst and cannot be limited, but is generally from 20° C. to 150° C. There is no particular restriction on the reaction pressure. That is, the reaction may be conducted at a reduced pressure, normal pressure, or an elevated pressure, but it is usually advantageous to conduct the reaction at normal pressure. Furthermore, the reaction time depends upon the kind of the raw materials, the amounts and the kinds of the catalyst and the promotor, the reaction temperature, etc., but is usually from about 5 to 200 hours.

Examples of the dihydric phenol compound represented by the formula (E) described above are bis(4-hydroxyphenyl)methane, bis(4-hydroxyphenyl) ether, bis(4-hydroxyphenyl) sulfone, bis(4-hydroxyphenyl) sulfoxide, bis(4-hydroxyphenyl) sulfide, bis(4-hydroxyphenyl) ketone, 1,1-bis(4-hydroxyphenyl)ethane, 2,2-bis(4-hydroxyphenyl)propane (bisphenol A; BPA), 2,2-bis(4-hydroxyphenyl)butane, 1,1-bis(4-hydroxyphenyl) cyclohexane (bisphenol Z; BPZ), 2,2-bis(4-hydroxy-3-chlorophenyl)propane, 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, α,ω-bis[3-(o-hydroxyphenyl)propyl]dimethylsilicone, and biphenol.

Examples of the carbonate precursor are phosgene and diaryl carbonates such as diphenyl carbonate, di-p-tolyl carbonate, phenyl-p-tolyl carbonate, di-p-chlorophenyl carbonate, dinaphthyl carbonate, etc.

The polymer of the present invention can be produced by a process similar to a conventional process which has been used to produce a polycarbonate from bisphenol A. For example, a process of directly reacting the dihydroxy compound, the dihydric phenol compound, and phosgene (phosgene process), a process of a transesterification of the dihydric phenol compound and a diaryl carbonate (transesterification process), etc., can be used.

In the phosgene process, the dihydroxy compound represented by the formula (D) described above is reacted with phosgene, or the dihydroxy compound represented by the formula (D) and the dihydric phenol compound represented by the formula (E) described above are reacted with phosgene usually in the presence of a catalyst and a solvent. Pyridine or an alkali metal hydroxide such as sodium hydroxide, potassium hydroxide, etc., is used as the catalyst, and methylene chloride, chloroform, chlorobenzene, xylene, etc., is used as the solvent.

It is preferable to conduct the reaction by adding a polymerization catalyst such as a tertiary amine (e.g., triethylamine), a quaternary ammonium salt, etc., to the reaction system to accelerate the condensation polymerization reaction or by adding a molecular weight modifier such as phenol, p-t-butylphenol, etc., to the reaction system to control the degree of polymerization. If desired, a small amount of an antioxidant such as sodium sulfite, hydrosulfite, etc., or a branching agent such as phloroglucine, isatinbisphenol, etc., may be added to the reaction system.

The reaction is conducted at a temperature of usually from 0° C. to 150° C., and preferably from 5° C. to 40° C. The reaction time depends upon the reaction temperature but is usually from 0.5 minute to 10 hours, and preferably from 1 minute to 2 hours. It is preferred that during the reaction, pH of the reaction system is maintained at at least 10.

On the other hand, in the transesterification process, a mixture of the dihydroxy compound represented by the formula (D) described above and a diaryl carbonate or a mixture of the dihydroxy compound represented by the formula (D), the dihydric phenol compound represented by the formula (E) described above, and a diaryl carbonate is reacted at a high temperature under reduced pressure. The reaction is conducted at a temperature range of usually from 150° C. to 350° C., and preferably from 200° C. to 300° C., and the final reaction pressure is reduced preferably below 1 mmHg, whereby phenols originated from the diaryl carbonate formed by the transesterification reaction are distilled off from the reaction system. The reaction time depends upon the reaction temperature and the reduced pressure but is usually from about 1 hour to 4 hours. It is preferred that the reaction is conducted under an inert gas atmosphere such as nitrogen gas, argon gas, etc. If desired, the reaction may be conducted with the addition of the molecular weight modifier, antioxidant, and branching agent described above.

The invention is described in more detail by the following examples, but the invention is not limited to those examples. Unless otherwise indicated, all parts, percents, ratios and the like are by weight.

Synthesis of Dihydroxy Compound Having Triphenylamine Structure

Example 1

To 1 mol (301 g) of bis(4-methylphenyl)-4-formylphenylamine was added 10 mols (940 g) of phenol and a hydrogen chloride gas was blown into the mixture with stirring while keeping the mixture at about 60° C. until the concentration of hydrochloric acid in the mixture became 2%. The reaction was continued for 8 hours. The hydrogen chloride gas was quickly removed from the reaction mixture under reduced pressure, and after the concentration of hydrochloric acid in the reaction mixture became 0.005%, the reaction mixture was cooled to 40° C. followed by filtration to obtain crystals of a dihydroxy compound having mixed therewith phenol.

The crystals were subjected to a vacuum distillation at about 30 mmHg and at 170° C. to remove phenol and the remaining crystals were sufficiently washed with methanol. The crystals were washed several times with water and dried under reduced pressure to obtain 312 g (yield 66.2%) of the dihydroxy compound having the structural formula (1) shown below.

It was identified by the elemental analysis, the IR spectral analysis, and the mass spectral analysis that the crystal thus obtained was the dihydroxy compound having the following structural formula (1). In addition, the identifications in other examples shown below were the same as above.

|  | C | H | N |
| --- | --- | --- | --- |
| Calculated: | 84.05% | 6.20% | 2.97% |
| Found: | 83.82% | 6.31% | 3.03% |

Elemental Analysis:

|  | C | H | N |
| --- | --- | --- | --- |
| Calculated: | 84.05% | 6.20% | 2.97% |
| Found: | 83.82% | 6.31% | 3.03% |

IR Spectra:

Near 3,300 cm$^{-1}$ (—OH)

A strong absorption was observed near 1,320 cm$^{-1}$ (aromatic tertiary amine)

A strong absortion was not observed near 1,700 cm$^{-1}$ (aromatic aldehyde).

Molecular Weight (m+): 471

Example 2

By following the same procedure as in Example 1 except that 1 mol (329 g) of bis(4-methylphenyl)-4-acetonylphenylamine was used in place of bis(4-methylphenyl)-4-formylphenylamine, 345 g (yield 70.9%) of the dihydroxy compound having structural formula (2) shown below was obtained.

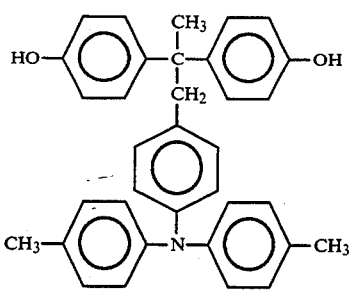

(2)

Elemental Analysis:

|  | C | H | N |
|---|---|---|---|
| Calculated: | 84.12% | 6.66% | 2.80% |
| Found: | 84.21% | 6.71% | 2.90% |

IR Spectra:
Near 3,300 cm$^{-1}$ (—OH)

A strong absorption was observed near 1,320 cm$^{-1}$ (aromatic tertiary amine)

A strong absorption was not observed near 1,700 cm$^{-1}$ (aliphatic ketone)

Molecular Weight (m+): 499

Example 3

By following the same procedure as in Example 1 except that 1 mol (315 g) of bis(4-methylphenyl)-4-acetylphenylamine was used in place of bis(4-methylphenyl)-4-formylphenylamine, 297 g (yield 61.2%) of the dihydroxy compound having the structural formula (3) shown below was obtained.

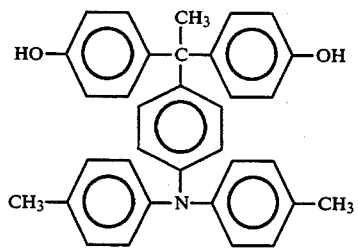

(3)

Elemental Analysis:

|  | C | H | N |
|---|---|---|---|
| Calculated: | 84.10% | 6.43% | 2.88% |
| Found: | 83.9% | 6.47% | 3.00% |

IR Spectra:
Near 3,300 cm$^{-1}$ (—OH)

A strong absorption was observed near 1,320 cm$^{-1}$ (aromatic tertiary amine)

A strong absorption was not observed near 1,700 cm$^{-1}$ (aromatic ketone)

Molecular Weight (m+): 485

Example 4

By following the same procedure as in Example 1 except that 1 mol (343 g) of bis(4-methylphenyl)-4-(3-oxobutyl)phenylamine was used in place of bis(4-methylphenyl)-4-formylphenylamine, 370 g (yield 72.1%) of the dihydroxy compound having the structural formula (4) shown below was obtained.

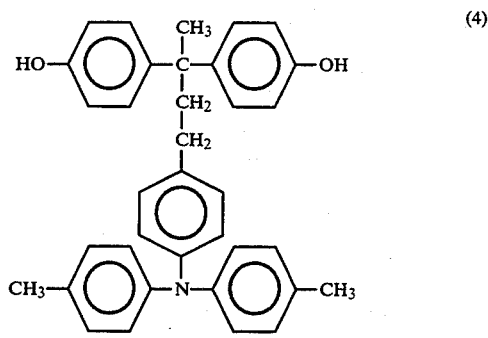

(4)

Elemental Analysis:

|  | C | H | N |
|---|---|---|---|
| Calculated: | 84.18% | 6.87% | 2.73% |
| Found: | 84.02% | 6.75% | 2.74% |

IR Spectra:
Mear 3,300 cm$^{-1}$ (—OH)

A strong absorption was observed near 1,320 cm$^{-1}$ (aromatic tertiary amine)

A strong abosrption was not observed near 1,700 cm$^{-1}$ (aliphatic ketone)

Molecular Weight (m+): 513

Example 5

By following the same procedure as in Example 1 except that 1 mol (600 g) of 1,3-bis[4-bis(4-methylphenyl)aminophenyl)-2-propanone was used in place of bis(4-methylphenyl)-4-formylphenylamine, 411 g (yield 53.4%) of the dihydroxy compound having the structural formula (5) shown below was obtained.

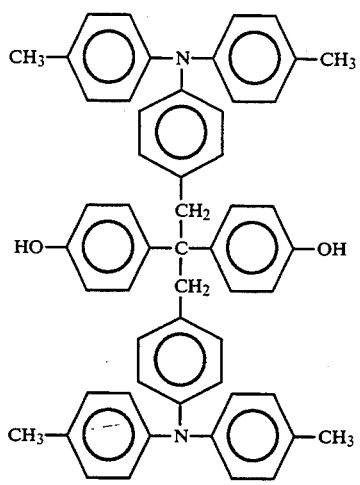

(5)

Elemental Analysis:

|  | C | H | N |
|---|---|---|---|
| Calculated: | 85.68% | 6.54% | 3.63% |
| Found: | 83.80% | 6.41% | 3.53% |

IR Spectra:

Near 3,300 cm$^{-1}$ (—OH)

A strong absorption was observed near 1,320 cm$^{-1}$ (aromatic tertiary amine)

A strong absorption was not observed near 1,700 cm$^{-1}$ (aliphatic ketone)

Molecular Weight (m+): 770

Example 6

By following the same procedure as in Example 1 except that 1 mol (403 g) of 9,9-dimethyl-2-[N-phenyl-N-(4-acetylphenyl)]aminofluorene was used in place of bis(4-methylphenyl)-4-formylphenylamine, 452 g (yield 78.8%) of the dihydroxy compound having the structural formula (6) shown below was obtained.

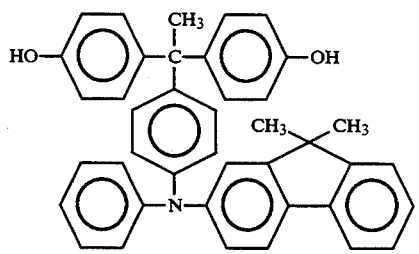

(6)

Elemental Analysis:

|  | C | H | N |
|---|---|---|---|
| Calculated: | 85.83% | 6.15% | 2.44% |
| Found: | 85.77% | 6.22% | 2.45% |

IR Spectra:

Near 3,300 cm$^{-1}$ (—OH)

A strong absorption was observed near 1,320 cm$^{-1}$ (aromatic tertiary amine)

A strong absorption was not observed near 1,700 cm$^{-1}$ (aliphatic ketone)

Molecular Weight (m+): 573

Example 7

By following the same procedure as in Example 1 except that 1 mol (403 g) of 4-[N-phenyl-N-(4-acetylphenyl)]amino-4'-methylstilbene was used in place of bis(4-methylphenyl)-4-formylphenylamine, 431 g (yield 75.2%) of the dihydroxy compound having the structural formula (7) shown below was obtained.

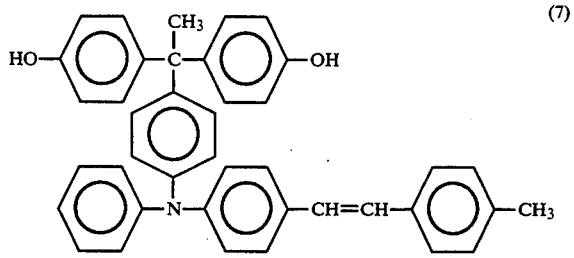

(7)

Elemental Analysis:

|  | C | H | N |
|---|---|---|---|
| Calculated: | 85.83% | 6.15% | 2.44% |
| Found: | 85.89% | 6.30% | 2.54% |

IR Spectra:

Near 3,300 cm$^{-1}$ (—OH)

A strong absorption was observed near 1,320 cm$^{-1}$ (aromatic tertiary amine)

A strong absorption was not observed near 1,700 cm$^{-1}$ (aliphatic ketone)

Molecular Weight (m+): 573

Example 8

By following the same procedure as in Example 1 except that 1 mol (439 g) of N-(4-acetylphenyl)-N,N-bis(4-biphenylyl)amine was used in place of bis(4-methylphenyl)-4-formylphenylamine, 406 g (yield 66.7%) of the dihydroxy compound having the structural formula (8) shown below was obtained.

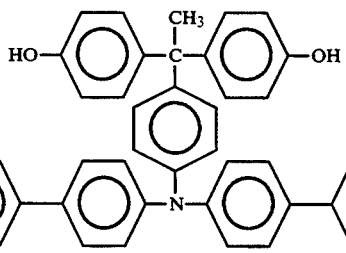

(8)

Elemental Analysis:

|  | C | H | N |
|---|---|---|---|
| Calculated: | 86.67% | 5.79% | 2.30% |
| Found: | 86.81% | 5.68% | 2.45% |

IR Spectra:

Near 3,300 cm$^{-1}$ (—OH)

A strong absorption was observed near 1,320 cm$^{-1}$ (aromatic tertiary amine)

A strong absorption was not observed near 1,700 cm$^{-1}$ (aliphatic ketone)
Molecular Weight (m+): 609

Production of Polymer

Example 9

In 580 ml of an aqueous solution of 8.8% (w/v) sodium hydroxide were dissolved 188.4 g of the dihydroxy compound having the triphenylamine structure of the structural formula (1) shown in Table 1 shown below and 0.1 g of hydrosulfite. To the solution was added 360 ml of methylene chloride, 2.0 g of p-t-butylphenol (PTBP) was added to the mixture with stirring while keeping the mixture at 15° C., and 51 g of phosgene was then introduced thereinto over a period of 60 minutes.

After completion of the introduction, the resulting mixture was stirred vigorously to emulsify the reaction mixture and after the emulsification, 0.2 ml of triethylamine was added to the emulsion followed by stirring for 1 hour to conduct the polymerization.

The polymer liquid thus formed was separated into an aqueous phase and an organic phase. The organic phase was neutralized with phosphoric acid and after repeatedly washing the organic phase with water until the pH of the washings became neutral, 470 ml of isopropanol was added thereto to precipitate the polymerized product. The precipitates were collected by filtration and dried to obtain a powdery polymer.

The limiting viscosity [η] of the solution of the polymer in methylene chloride as a solvent at a concentration of 0.5 g/dl at a temperature of 20° C. was 0.46 dl/g.

As a result of analyzing the polymer obtained by the infrared absorption spectra, the absorption by a carbonyl group was observed at the position of 1,770 cm$^{-1}$ and the absorption of an ether bond was observed at the position of 1,240 cm$^{-1}$. Consequently it was confirmed that the polymer had a carbonate bond. Also, the absorptions originated from a hydroxy group were not substantially observed at the positions of 3,650 cm$^{-1}$ to 3,200 cm$^{-1}$.

Thus, the polymer was confirmed to be a polycarbonate polymer composed of the repeating unit shown in Table 1 below.

Example 10

The same procedure as in Example 9 was followed except that 199.6 g of the dihydroxy compound of the structural formula (2) shown in Table 1 below was used in place of the dihydroxy compound of the structural formula (1).

The limiting viscosity [η] of the polymer obtained was 0.46 dl/g and from the infrared absorption spectral analysis of the polymer, the polymer was confirmed to be a polycarbonate polymer having the repeating unit shown in Table 1 below.

Example 11

The same procedure as in Example 9 was followed except that 194 g of the dihydroxy compound of the structural formula (3) shown in Table 1 below was used in place of the dihydroxy compound of the structural formula (1).

The limiting viscosity [η] of the polymer obtained was 0.46 dl/g and from the infrared absorption spectral analysis of the polymer, the polymer was confirmed to be a polycarbonate polymer having the repeating unit shown in Table 1 below.

Example 12

The same procedure as in Example 9 was followed except that 205.2 g of the dihydroxy compound of the structural formula (4) shown in Table 1 below was used in place of the dihydroxy compound of the structural formula (1).

The limiting viscosity [η] of the polymer obtained was 0.46 dl/g and from the infrared absorption spectral analysis of the polymer, the polymer was confirmed to be a polycarbonate polymer having the repeating unit shown in Table 1 below.

Example 13

The same procedure as in Example 9 was followed except that 308 g of the dihydroxy compound of the structural formula (5) shown in Table 1 below was used in place of the dihydroxy compound of the structural formula (1).

The limiting viscosity [η] of the polymer obtained was 0.48 dl/g and from the infrared absorption spectral analysis of the polymer, the polymer was confirmed to be a polycarbonate polymer having the repeating unit shown in Table 1 below.

Example 14

The same procedure as in Example 9 was followed except that 99.8 g of the dihydroxy compound of the structural formula (2) shown in Table 1 below and 45.6 g of bisphenol A were used in place of the dihydroxy compound of the structural formula (1).

The limiting viscosity [η] of the polymer obtained was 0.46 dl/g and from the infrared absorption spectral analysis of the polymer, the polymer was confirmed to be a polycarbonate polymer having the repeating unit shown in Table 1 below.

TABLE 1

| Dihydroxy Compound Used | Product |
| --- | --- |
| Example 9 (1) 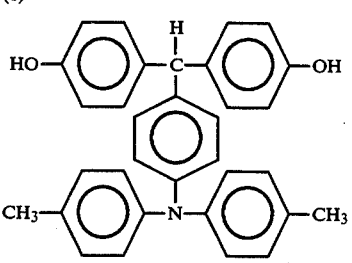 | 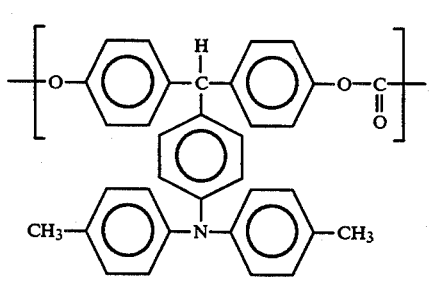 |

TABLE 1-continued

| Dihydroxy Compound Used | Product |
|---|---|
| Example 10 (2) | |
| Example 11 (3) | |
| Example 12 (4) | |
| Example 13 (5) | |
| Example 14 | |

TABLE 1-continued

| Dihydroxy Compound Used | Product |
|---|---|
| Structure (2) of Example 10 and bisphenol A | 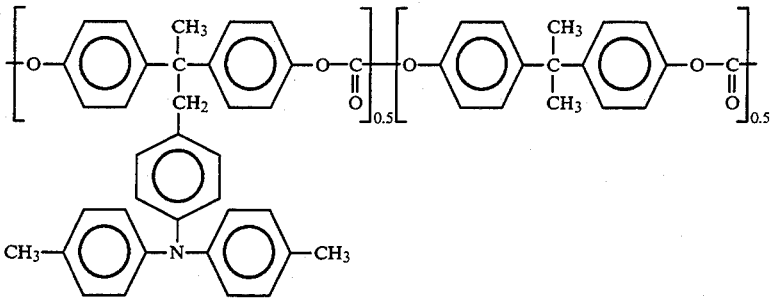 |

Example 15

The same procedure as in Example 9 was followed except that 229.2 g of the dihydroxy compound having the following structural formula (6) was used in place of the dihydroxy compound of the structural formula (1).

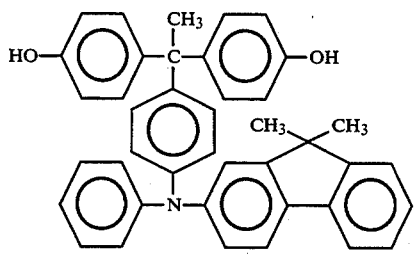

(6)

The limiting viscosity [$\eta$] of the polymer obtained was 0.46 dl/g and from the infrared absorption spectral analysis of the polymer, the polymer was confirmed to be a polycarbonate polymer having the repeating unit having the structure shown below.

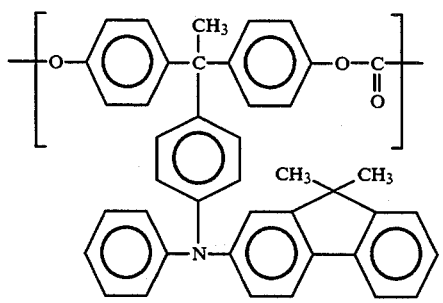

Example 16

The same procedure as in Example 9 was followed except that 229.2 g of the dihydroxy compound having the following structural formula (7) was used in place of the dihydroxy compound of the structural formula (1).

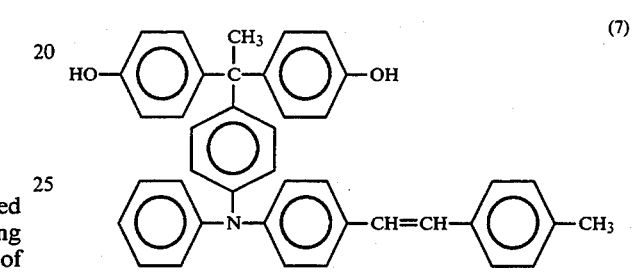

(7)

The limiting viscosity [$\eta$] of the polymer obtained was 0.47 dl/g and from the infrared absorption spectral analysis of the polymer, the polymer was confirmed to be a polycarbonate polymer having the repeating unit having the following structure.

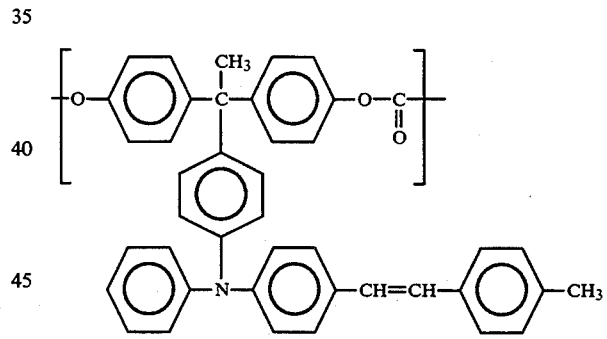

Example 17

The same procedure as in Example 9 was followed except that 243.6 g of the dihydroxy compound having the following structure (8) was used in place of the dihydroxy compound of the structural formula (1).

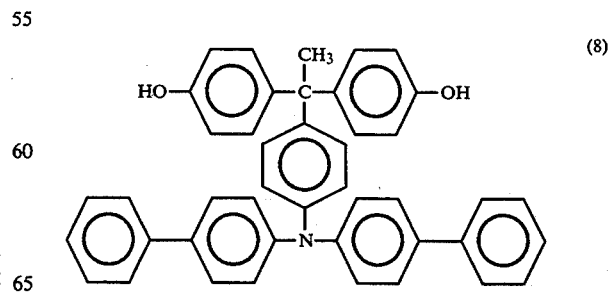

(8)

The limiting viscosity [$\eta$] of the polymer obtained was 0.47 dl/g and from the infrared absorption spectral analysis of the polymer, the polymer was confirmed to be a polycarbonate polymer having the repeating unit having the following structure.

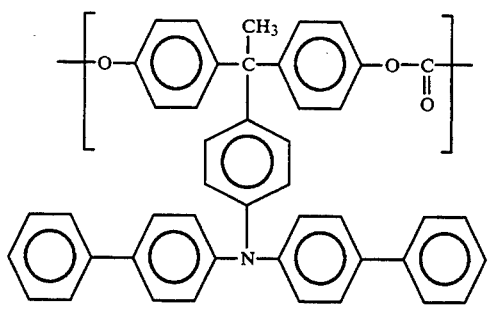

While the invention has been described in detail and with reference to specific examples thereof, it will be apparent to one skilled in the art that various changes and modifications can be made therein without departing from the spirit and scope thereof.

What is claimed is:

1. An aromatic polycarbonate comprising a repeating unit represented by the following formula (A) derived from a dihydroxy compound having a triphenylamine structure represented by the following formula (D) or comprising the repeating unit represented by the following formula (A) and a repeating unit represented by the following formula (C) derived from a dihydric phenol compound represented by the following formula (E), the molar ratio of the repeating unit represented by the formula (A) being $0<(A)/[(A)+(C)]\leq 1$;

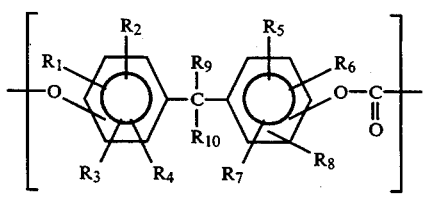
(A)

wherein $R_1$ to $R_8$ each represents hydrogen atom, a halogen atom, an alkoxy group, an alkyl group which may have a substituent, an alkenyl group which may have a substituent, or an aryl group which may have a substituent and one of $R_9$ and $R_{10}$ represents a group containing a triphenylamine represented by the following formula (B) and the other thereof represents hydrogen atom, an alkyl group, an alkenyl group, or an aryl group, each group may have a substituent, or both of $R_9$ and $R_{10}$ represent the group containing the triphenylamine represented by the following group (B);

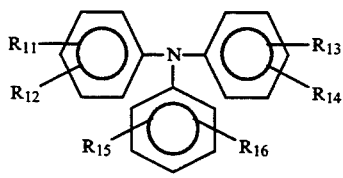
(B)

wherein $R_{11}$ to $R_{16}$ each represents hydrogen atom, a halogen atom, an alkyl group, an alkoxy group, an alkenyl group, an aryl group, an arylamino group, an aryl ether group, or an aminoaryl ether group, each group may have a substituent, or $R_{11}$ and $R_{12}$, $R_{13}$ and $R_{14}$, or $R_{15}$ and $R_{16}$ represent groups which combine with each other to form a carbon ring or a heterocyclic ring, and one of $R_{11}$ to $R_{16}$ becomes a divalent group, which combines to $-(CH_2)_a-$ (wherein a represents an integer of from 0 to 5) to form the group shown by $R_9$ or $R_{10}$ in the formula (A) described above;

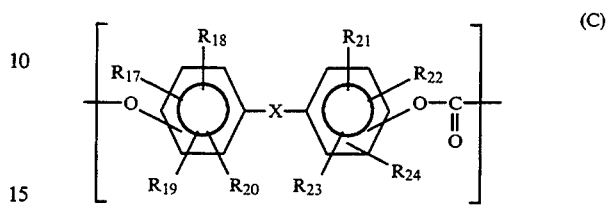
(C)

wherein $R_{17}$ to $R_{24}$ each represents hydrogen atom, a halogen atom, an alkyl group, or an aryl group, each group may have a substituent and X represents

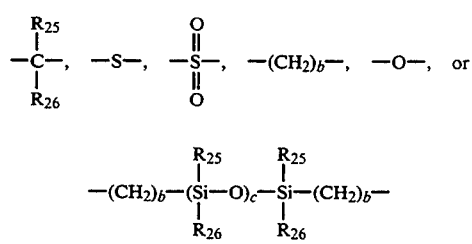

wherein $R_{25}$ and $R_{26}$ each represents hydrogen atom, a halogen atom, an alkyl group, or an aryl group, each group may have a substituent or $R_{25}$ and $R_{26}$ represent groups which combine together to form a carbon ring or a heterocyclic ring; b represents an integer of from 0 to 20; and c represents an integer of from 0 to 2,000;

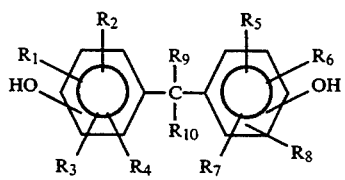
(D)

wherein $R_1$ to $R_{10}$ are the same as defined in the formula (A) described above;

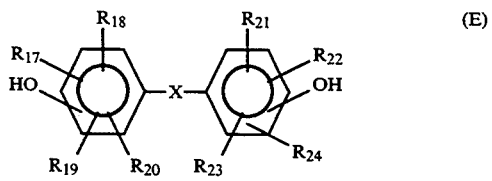
(E)

wherein $R_{17}$ to $R_{24}$ and X are the same as defined in the formula (C) described above.

2. An aromatic polycarbonate as calmed in claim 1, wherein the dihydroxy compound having the triphenylamine structure represented by the formula (D) is at least one selected from the group consisting of the compounds represented by the following formulae (1) to (8);

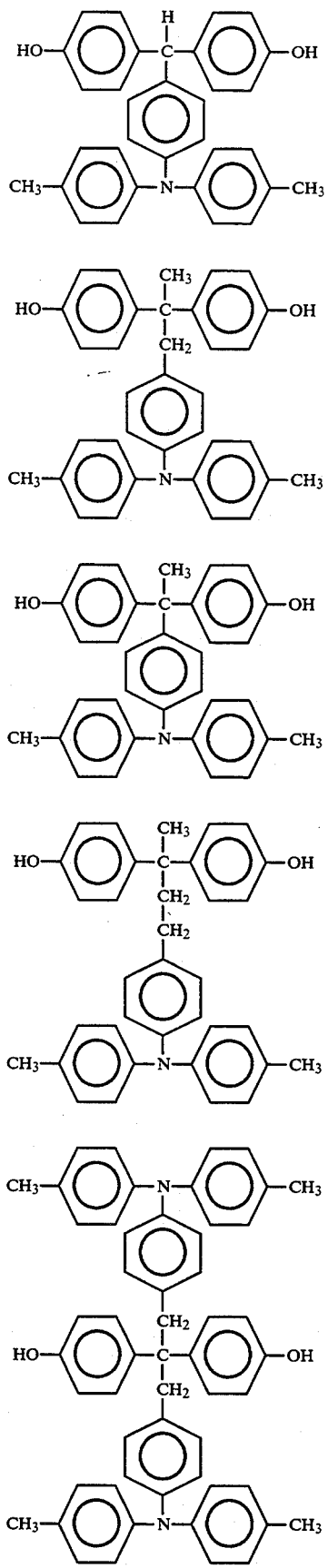
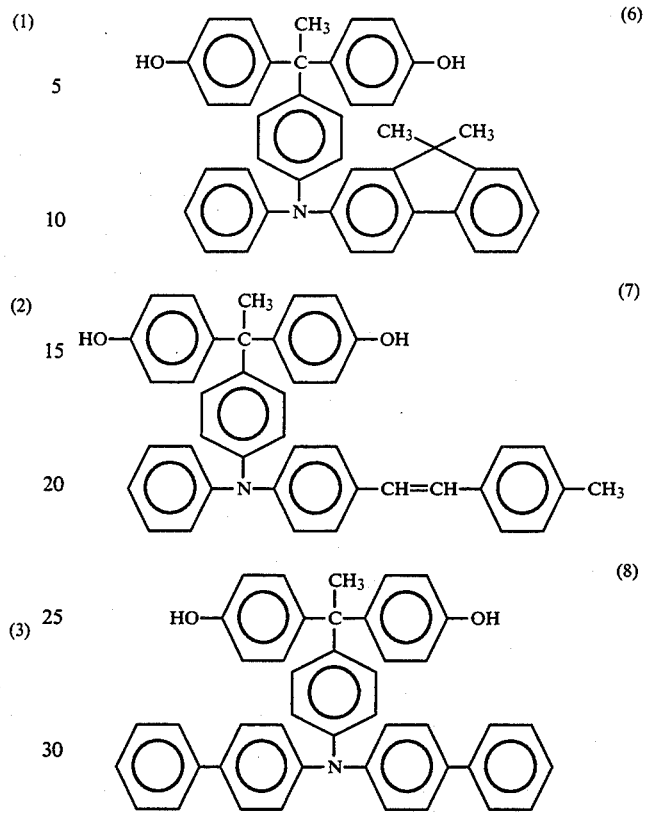

3. An aromatic polycarbonate as claimed in claim 1, wherein the dihydric phenol compound represented by the formula (E) is at least one selected from the group consisting of his (4-hydroxyphenyl)methane, bis(4-hydroxyphenyl) ether, bis(4-hydroxyphenyl) sulfone, bis(4-hydroxyphenyl) sulfoxide, bis(4-hydroxyphenyl) sulfide, bis(4-hydroxyphenyl) ketone, 1,1-bis(4-hydroxyphenyl) ethane, 2,2-bis(4-hydroxyphenyl)propane, 2,2-bis (4-hydroxy-3,5-dimethylphenyl)propane, 2,2-bis(4-hydroxyphenyl)butane, 1,1-bis(4-hydroxyphenyl)cyclohexane, 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis (4-hydroxy-3-methylphenyl)propane, 1,1-bis(4-hydroxyphenyl)-1-phenylethane, bis(4-hydroxyphenyl)diphenylmethane, α,ω-bis[3-(o-hydroxyphenyl)propyl]dimethylsilicone, and biphenol.

4. An aromatic polycarbonate as claimed in claim 1, wherein the dihydric phenol compound represented by the formula (E) is at least one selected from the group consisting of bis (4-hydroxyphenyl)methane, 2,2-bis(4-hydroxyphenyl)propane, 2,2-bis(4-hydroxyphenyl)butane, 1,1-bis(4-hydroxyphenyl)cyclohexane, 2,2-bis(4-hydroxy-3,5-dibromophenyl)propane, 2,2-bis(4-hydroxy-3,5-dichlorophenyl)propane, and 1,1-bis(4-hydroxyphenyl)ethane.

5. A process for of producing an aromatic polycarbonate comprising a repeating unit represented by the following formula (A), which comprises reacting a dihydroxy compound having a triphenylamine structure represented by the following formula (D) and a carbonate precursor in the presence of a catalyst and a solvent;

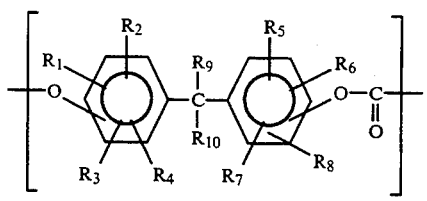

(A)

wherein $R_1$ to $R_8$ each represents hydrogen atom, a halogen atom, an alkoxy group, an alkyl group which may have a substituent, an alkenyl group which may have a substituent, or an aryl group which may have a substituent and one of $R_9$ and $R_{10}$ represents a group containing a triphenylamine represented by the following formula (B) and the other thereof represents hydrogen atom, an alkyl group, an alkenyl group, or an aryl group, each group may have a substituent or both of $R_9$ and $R_{10}$ represent a group containing the triphenylamine represented by the following formula (B);

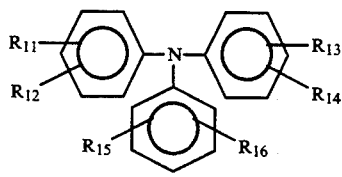

(B)

wherein $R_{11}$ to $R_{16}$ each represents hydrogen atom, a halogen atom, an alkyl group, an alkoxy group, an alkenyl group, an aryl group, an arylamino group, an aryl ether group, or an aminoaryl ether group, each group may have a substituent, or said $R_{11}$ and $R_{12}$, said $R_{13}$ and $R_{14}$, or said $R_{15}$ and $R_{16}$ represents groups which combine with each other to form a carbon ring or a heterocycic ring, and one of $R_{11}$ to $R_{16}$ becomes a divalent group and combines with —$(CH_2)_a$— (wherein a represents an integer of from 0 to 5) to form the group shown by $R_9$ or $R_{10}$ of the formula (A);

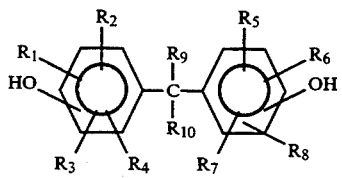

(D)

wherein $R_1$ to $R_{10}$ are the same as defined in the formula (A) described above.

6. A process for producing an aromatic polycarbonate as claimed in claim 5, wherein the carbonate precursor is phosgene, diphenyl carbonate, di-p-tolyl carbonate, phenyl-p-tolyl carbonate, di-p-chlorophenyl carbonate, or dinaphthyl carbonate.

7. A process for producing an aromatic polycarbonate as claimed in claim 5, wherein the carbonate precursor is phosgene.

8. A process for producing an aromatic polycarbonate as claimed in claim 5, wherein the catalyst is pyridine, sodium hydroxide, or potassium hydroxide.

9. A process for producing a polycarbonate as claimed in claim 5, wherein the reaction is conducted in the presence of at least one polymerization catalyst selected from the group consisting of tertiary amines and quaternary ammonium salts.

10. A process for producing a polycarbonate comprising a repeating unit represented by the following formula (A) and a repeating unit represented by the following formula (C), which comprises reacting a dihydroxy compound having a triphenylamine structure represented by the formula (D), a dihydric phenol compound represented by the following formula (E), and a carbonate precursor in the presence of a catalyst and a solvent;

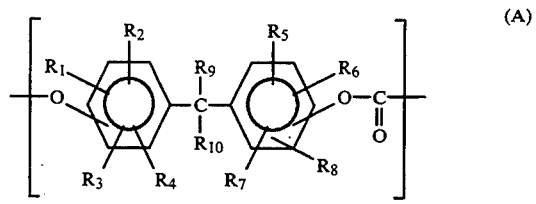

(A)

wherein $R_1$ to $R_8$ each represents hydrogen atom, a halogen atom, an alkoxy group, an alkyl group which may have a substituent, an alkenyl group which may have a substituent, or an aryl group which may have a substituent and one of $R_9$ and $R_{10}$ represents a group containing a triphenylamine represented by the following formula (B) and the other thereof represents hydrogen atom, an alkyl group, an alkenyl group, or an aryl group, each group may have a substituent, or both of $R_9$ and $R_{10}$ represent the group containing the triphenylamine represented by the formula (B);

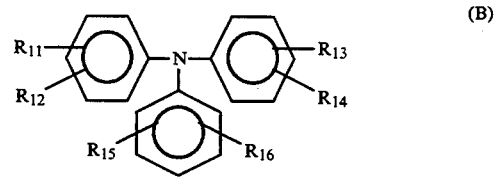

(B)

wherein $R_{11}$ to $R_{16}$ each represents hydrogen atom, a halogen atom, an alkyl group, an alkoxy group, an alkenyl group, an aryl group, an arylamino group, an aryl ether group, or an aminoaryl ether group, each group may have a substituent, or said $R_{11}$ and $R_{12}$, said $R_{13}$ and $R_{14}$, or said $R_{15}$ and $R_{16}$ represent groups which combine with each other to form a carbon ring or a heterocyclic ring, and one of $R_{11}$ to $R_{16}$ becomes a divalent group and combines with —$(CH_2)_a$— (wherein a represents an integer of from 0 to 5) to form the group shown by $R_9$ or $R_{10}$ of the formula (A);

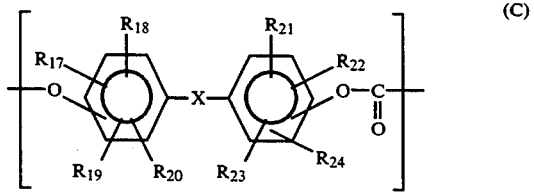

(C)

wherein $R_{17}$ to $R_{24}$ each represents hydrogen atom, a halogen atom, an alkyl group or an aryl group, each group may have a substituent and X represents

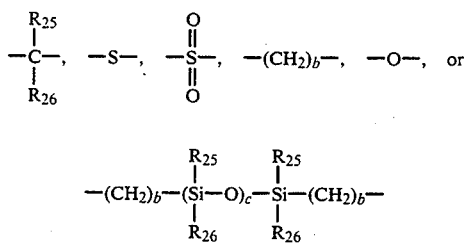

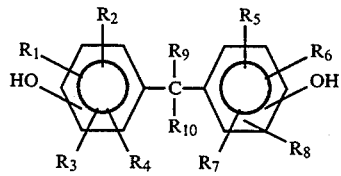

wherein $R_{25}$ and $R_{26}$ each represents hydrogen atom, a halogen atom, an alkyl group, or an aryl group, each group may have a substituent or $R_{25}$ and $R_{26}$ represent groups which combine with each other to form a carbon ring or a heterocyclic ring; b represents an integer of from 0 to 20; and c represents an integer of from 0 to 2,000;

(D)

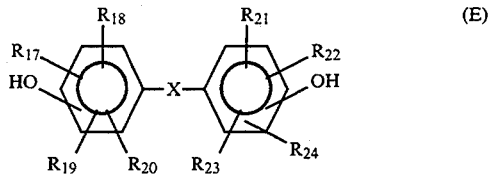

wherein $R_1$ to $R_{10}$ are the same as defined in the formula (A) described above;

(E)

wherein $R_{17}$ to $R_{24}$ and X are the same as defined in the formula (C) described above.

11. A process for producing an aromatic polycarbonate as claimed in claim 10, wherein the carbonate precursor is phosgene, diphenyl carbonate, di-p-tolyl carbonate, phenyl-p-tolyl carbonate, di-p-chlorophenyl carbonate, or dinaphthyl carbonate.

12. A process for producing an aromatic polycarbonate as claimed in claim 10, wherein the carbonate precursor is phosgene.

13. A process for producing an aromatic polycarbonate as claimed in claim 10, wherein the catalyst is pyridine, sodium hydroxide, or potassium hydroxide.

14. A process for producing an aromatic polycarbonate as claimed in claim 10, wherein the reaction is conducted in the presence of at least one polymerization catalyst selected from the group consisting of tertiary amines and quaternary ammonium salts.

* * * * *